(12) United States Patent
Glatkowski et al.

(10) Patent No.: US 6,986,853 B2
(45) Date of Patent: Jan. 17, 2006

(54) CARBON NANOTUBE FIBER-REINFORCED COMPOSITE STRUCTURES FOR EM AND LIGHTNING STRIKE PROTECTION

(75) Inventors: Paul J. Glatkowski, Littleton, MA (US); David H. Landis, Barrington, RI (US); Joseph W. Piche, Raynham, MA (US); Jeffrey L. Conroy, Rumford, RI (US)

(73) Assignee: Eikos, Inc., Franklin, MA (US)

( * ) Notice: Subject to any disclaimer, the term of this patent is extended or adjusted under 35 U.S.C. 154(b) by 98 days.

(21) Appl. No.: 10/105,622

(22) Filed: Mar. 26, 2002

(65) Prior Publication Data

US 2002/0180077 A1 Dec. 5, 2002

Related U.S. Application Data

(60) Provisional application No. 60/278,417, filed on Mar. 26, 2001.

(51) Int. Cl.
*B29C 73/00* (2006.01)

(52) U.S. Cl. .................. 264/36.19; 264/36.2; 264/104; 264/267

(58) Field of Classification Search ............... 264/36.1, 264/36.18, 36.19, 36.22, 104, 105, 250, 254, 264/267, 273; 252/502, 511; 428/299.1; 427/97.8, 427/122, 97
See application file for complete search history.

(56) References Cited

U.S. PATENT DOCUMENTS

| | | | |
|---|---|---|---|
| 4,409,270 A | * | 10/1983 | Faber et al. ................... 428/63 |
| 4,580,874 A | * | 4/1986 | Winter et al. .................. 385/99 |
| 4,775,501 A | * | 10/1988 | Rosenzweig et al. ....... 264/450 |
| 5,292,854 A | | 3/1994 | Keller |
| 5,547,525 A | | 8/1996 | Bennett et al. |
| 5,560,898 A | | 10/1996 | Uchida et al. |
| 5,640,705 A | | 6/1997 | Koruga |
| 5,695,734 A | | 12/1997 | Ikazaki et al. |
| 5,753,088 A | | 5/1998 | Olk |
| 5,773,834 A | | 6/1998 | Yamamoto et al. |
| 5,849,830 A | | 12/1998 | Tsipursky et al. |
| 5,853,877 A | | 12/1998 | Shibuta |
| 5,908,585 A | * | 6/1999 | Shibuta ...................... 252/506 |
| 5,935,360 A | * | 8/1999 | Griggs ......................... 156/94 |
| 5,939,508 A | | 8/1999 | Keller |
| 5,965,202 A | | 10/1999 | Taylor-Smith et al. |
| 6,031,711 A | | 2/2000 | Tennent et al. |
| 6,038,060 A | | 3/2000 | Crowley |
| 6,099,965 A | | 8/2000 | Tinnent et al. |
| 6,124,365 A | | 9/2000 | Lan et al. |
| 6,146,227 A | * | 11/2000 | Mancevski ................... 445/24 |
| 6,205,016 B1 | | 3/2001 | Niu |
| 6,250,984 B1 | | 6/2001 | Jin et al. |
| 6,265,466 B1 | | 7/2001 | Glatkowski et al. |
| 6,280,677 B1 | | 8/2001 | Yakobson |
| 6,283,812 B1 | | 9/2001 | Jin et al. |
| 6,299,812 B1 | | 10/2001 | Newman et al. |
| 6,322,730 B1 | * | 11/2001 | Wachtler ................. 264/36.22 |
| 6,333,016 B1 | | 12/2001 | Resasco et al. |
| 6,350,516 B1 | | 2/2002 | Weber et al. |
| 6,355,203 B1 | * | 3/2002 | Charmes et al. ............ 264/493 |
| 6,395,199 B1 | * | 5/2002 | Krassowski et al. ........ 252/511 |
| 6,426,134 B1 | * | 7/2002 | Lavin et al. ............. 428/300.1 |
| 6,597,090 B1 | * | 7/2003 | Mancevski .................. 313/309 |

FOREIGN PATENT DOCUMENTS

| | | |
|---|---|---|
| EP | 0 949 199 A1 | 10/1999 |
| JP | 01022982 | 1/1989 |
| JP | 64-22982 | 1/1989 |
| WO | WO 99/65821 | 12/1999 |
| WO | WO 01/92381 | 12/2001 |

OTHER PUBLICATIONS

Peter Fairley, "Nanotechnology: The Start of Something Big," Chemicalweek pp. 23–26 (Dec. 12, 2001).
Pulickel M. Ajayan, "Aligned Carbon Nanotubes in a Thin Polymer Film," Advanced Materials, vol. 7, No. 5, pp. 489–491 (1995).
J. Sandler et al., "Development of a Dispersion Process for Carbon Nanotubes in an Epoxy Matrix and the Resulting Electrical Properties," Polymer 40, pp. 5967–5971 (1999).
Kevin Ausman et al., "Organic Solvent Dispersions of Single–Walled Carbon Nanotubes: Toward Solutions of Pristine Nanotubes," Journal of Physical Chemistry, vol. 104, No. 38, pp. 8911–8915 (Sep. 28, 2000).
Philip Ball, "Through the Nanotube," New Scientist, pp. 28–31 (Jul. 6, 1996).
B.I. Yakobson et al., "Fullerene Nanotubes: $C_{1,000,000}$ and Beyond," American Scientist, vol. 85, pp. 324–337 (Jul.–Aug. 1997).
P.M. Ajayan et al., "Nanometre–size tubes of carbon," Rep. Prog. Phys., vol. 60, pp. 1025–1062 (1997).

* cited by examiner

Primary Examiner—Angela Ortiz
(74) Attorney, Agent, or Firm—Powell Goldstein LLP

(57) ABSTRACT

A method for repairing fiber-reinforced composite structures while maintaining original EM and lightning protection using carbon nanotubes, fibers, and thermoset resins is disclosed. According to one embodiment of the invention, the method comprises preparing a damaged area for repair; preparing a repair patch for the damaged area, the repair patch comprising nanotubes; applying the repair patch to the damaged area; and curing the repair patch. A repair patch for a composite structure having a conductive layer is disclosed. According to one embodiment of the present invention, the repair patch includes a binder and nanotubes. A repair resin for repairing a composite structure having a conductive layer is disclosed. According to one embodiment of the present invention, the repair layer includes a resin and nanotubes. A putty for repairing a composite structure having a conductive layer is disclosed. According to one embodiment of the present invention, the putty includes a base and electrically conductive carbon nanotubes.

9 Claims, No Drawings

CARBON NANOTUBE FIBER-REINFORCED COMPOSITE STRUCTURES FOR EM AND LIGHTNING STRIKE PROTECTION

RELATION TO OTHER APPLICATIONS

This application claims priority to U.S. Provisional Application No. 60/278,417 entitled "Method for Repairing Fiber-Reinforced Composite Structures while Maintaining Original EMI and Lightning Protection using Carbon Nanotubes, Fibers, and Thermoset Resins" filed Mar. 26, 2001, which is entirely incorporated by reference.

RIGHTS IN THE INVENTION

This invention was made, in part, with support from the United States Government and the United States may have rights to the invention.

BACKGROUND OF THE INVENTION

1. Field of the Invention

The present invention relates to compositions and methods for the manufacture and repair of composite structures that contain conductive layers and, more particularly, to methods using nanotubes for manufacturing and repairing fiber-reinforced composite structures that provide and maintain EM and lightning protection.

2. Description of the Background

Composite structures that contain conductive layers to impart electromagnetic (EM) and lightning strike protection to the structure are known in the art. These composites can function alone, or in conjunction with other structural parts, to protect an entire enclosure. Typically, these types of composites may be found in fiber-reinforced polymer matrix composite walls, decks, roofs of a building, ships, vehicles, aerospace crafts, electrical housings, etc. In addition to the mechanical benefits of using such composite structures, the fabrication of these structures provides an electrically conductive layer that protects the structure from damage from lightening strikes (see publication numbers MIL-HDBK-1004/6, 1988; AD-A 252 281, 1992; NRL/MR1465492-6986) and transmission of broadband EM radiation.

The protective conductive layer is installed during the fabrication of the structure and remains functional until damaged. Damage can result from a lightning strike, or mechanical impact or stress from deliberate enemy attack. Resulting damage can be exhibited as a crack or hole, or any separation that interrupts electrical conductivity in the area of the damage, which thereby allows the transmission of EM and reduces the conductive pathway for mitigation of lightening strike.

Known techniques used to repair the structure's electrical and mechanical properties typically involve cutting the damaged area from the structure, routing the hole to form steps at each layer of the composite, and filling the whole with new layers of fiber and resin. For an example of such a process, see Composite Repair, available from Fibre Glast Developments Corporation, Brookville, Ohio.

If the conductive layer is included in the repair patch, that patch must make electrical contact to the electrical layer existing in the damaged structure to provide the same layer of EM and lightening protection as the original structure. The electrically conductive layer in the structure typically includes conductive materials, such as metal-coated fibers of carbon, glass, or polymers, foils of metals, and screens of metals. Electromagnetic materials, and their properties, are known in the art. See Neelakanta, Perambur S. *Handbook of Electromagnetic Materials*, CRC Press, Inc., New York, 1995. Once the layers of the composite are damaged, however, making electrical contact with the metal coating on the fibers forming the protective layer is very difficult and often practically impossible such that the damaged structure is considered damaged beyond repair and an entirely new structure must be manufactured.

In traditional patch repair techniques, the two conductive layers have only incidental contact wherever the conductive fibers happened to make contact, even if some effort is made to commingle the fibers from the patch to those in the structure. Exposure of the structures conductive a fiber is very difficult and does not guarantee that contact between the repair fiber and the structure will occur during cure and final assemble of the other nonconductive (structural) layers of the patch.

The level of difficulty of the repair is greatly increased when such repairs must be conducted during armed conflicts, such as in the repair of a naval ship during battle. The damaged ship is both more vulnerable to attack and less capable of defending itself due to the loss of EM protection.

SUMMARY OF THE INVENTION

A need has arisen for compositions and methods for the manufacture and repair of fiber-reinforced composite structures that provide EM and lightning protection.

One embodiment of the invention is directed to methods for the manufacture of composite structures using nanotubes that provide EM and lightning protection to the structure. The method comprises preparing composite to include nanotubes that impart a conductivity to the composite and, optionally, curing the nanotube-containing composite. Structures damaged by EM, lightning or other electrical energy can be repaired quickly and efficiently, and without the need for elaborate patching. Further, due to the presence of nanotubes, it may not be necessary to repair the structure at all to maintain sufficient and continued protection from lightning and other violet discharges of energy.

Another embodiment of the invention is directed to methods for the repair of composite structures using nanotubes that impart or maintain existing EM and lightning protection to the structure. The method comprises preparing a damaged area for repair; preparing a repair patch comprising nanotubes that provide an electrically conductive layer for forming to the damaged area; applying the repair patch to the damaged area; and, optionally, curing the repair patch. The repair patch may be comprised of composite material of the damaged area, binder material, and carbon nanotubes. Alternatively, the repair patch may be comprised of putty or another moldable material plus carbon nanotubes that can be simply pressed and molded into the damaged area.

Another embodiment of the invention is directed to nanotube-containing resins and putties for the manufacture and/or repair of composite structures. The materials allow for efficient repair and maintain or impart an electrically conductive function that overcomes a hole or separation within the structure.

Another embodiment of the invention is directed to methods for the manufacture and/or repair of the mechanical and electrical portions of composite structure. Manufacture or repair of mechanical aspects are performed using traditional techniques with the inclusion or substitution of nanotube filled resins and chopped fibers. Fibers may be metallic or other electrically conductive substances that allow for contact between a patch and a damaged area of a structure.

Another embodiment of the invention is directed to layers comprising electrically conductive nanotubes that can be pressed into damaged areas of a composite structure. Layers may be moldable and/or precut to desired lengths and sizes for application as patches to damaged areas of a composite structure. A single or plurality of layers may be composed of composite material or precursor materials that require curing for sealing to a damaged structure. Alternatively, one or more layers may be films or coatings that are added or applied to composite structures to allow for future repair with carbon nanotube containing materials.

Other embodiments and advantages of the invention are set forth, in part, in the following description and, in part, may be obvious from this description, or may be learned from the practice of the invention.

DESCRIPTION OF THE INVENTION

The present invention overcomes the problems identified in the prior art by incorporating carbon nanotubes into composite structure including binder resins, putties, insertion layers and other components of a composite structure forming conductive layers in the structure and/or a composite patch necessary or helpful to facilitate repairs.

It was surprisingly discovered that the presence of nanotubes in the structure or repair materials imparts electrical conductivity to those materials, which, in turn, facilitates electrical continuity between conductive fibers in the structure. When damaged, these structures can be easily repaired with patches containing nanotubes that allow for formation of conductive layers between the patch and the structure. The presence of the nanotube alone without the conductive fiber also provides some electrical protection, such as EM and lightning strike protection; however, the addition of the conductive fibers enhances the electrical conductivity, electrical current carrying capacity such as for lightening protection, and increases the likelihood of direct fiber-to-fiber contact in the final repair.

Composite structure to which can be applied the methods and compositions of the invention include, but are not limited to, aircraft parts, automobile parts, electrical device housings, support structures, walls of enclosures, and combinations thereof. These composites may be comprised of a large variety of many different polymers, metals, plastic compounds, and other such support materials. Typically, these materials house instruments and other devices that are electrically sensitive and subject to damage upon exposure to electrical energy such as from a lightning strike, electromagnetic (EM) radiation or other electrical discharge. Composites of the invention may uniformly or non-uniformly comprise carbon nanotubes within their matrix or other electrically conductive fibers. Alternatively, composite structure may be coated with carbon nanotube containing paint. Preferably, the coating at least partially and more preferably totally encompasses the composite structure to provide complete protection of the structure or devices contained within the structure from external electrical energy. In addition, the composite structure itself may be the electrically sensitive material, not necessarily because it contains electrically sensitive instruments, but because it conducts electrical energy such as the exterior or an airplane.

Preferably, the carbon nanotubes or other electrically conductive fibers (e.g. chopped fibers) are within the composite structure, the resin, a putty used to repair the structure, or are within an insert or layer to be applied to the damaged area. Carbon nanotubes are preferably present in the composite structure at less than 20%, preferably less than 10%, more preferably less than 2%, and still more preferably at less than 0.5%. Carbon nanotubes are preferably present in putties, resins and individual layers at greater than 25%, preferably greater than 50%, more preferably greater than 75%, still more preferably greater than 90%. Still more preferably, the repair materials are pure carbon nanotubes. Alternatively, the repair materials may comprise carbon nanotubes and additional chemicals such as carbon black, buckeyballs, fullerenes or other electrically conductive materials such as organic or inorganic metal compounds (e.g. indium tin oxides, zinc oxides). Such materials contain typically contain carbon at greater than 25%, preferably greater than 50%, more preferably greater than 75%, still more preferably greater than 90%. Still more preferably, the repair materials are comprised of all carbon.

Layers of carbon nanotubes or insert materials, at most any percentage of carbon, can further comprise moldable agents such as putties and plasticizers that allow for the layer to be molded to the damaged area thereby creating a tight fit between the layer and the structure. Additional composite material can be pressed into the damaged area covered by the layer to further seal and provide desired structural support to the damaged composite structure.

Successful manufacture and/or repair of an electrically-conductive structure depends on bridging the gap between the conductive fibers layer in the structure and those in the repair patch. By incorporating the nanotube into the original structure prior to damage, the area with which to make electrical contact is enlarged, thereby facilitating contact with the repair patch layers. The repair patch conductive fiber layer may also be immersed in a layer of resin that may be include nanotubes. Further, putty may be used to fill any gap in this region. In one embodiment, the putty may be composed of resin, chopped fibers (conductive or nonconductive) such as metal or carbon particles, and electrically conductive carbon nanotubes. To further facilitate the repair, the layer of resin containing the conductive fibers in the structure may contain carbon nanotubes, and may be easily removed by through dissolution, or etching, with a predetermined solution in order to remove the resin that surrounds the conductive fibers in the area/region/edge of repair. The removal of resin surrounding the fibers exposes more of the fibers metal surface, and the increased surface area consequently increases the likelihood of establishing a low-resistance electrical contact with those fibers in the repair patch or the putty.

One method for repairing fiber-reinforced composite structures, according to one embodiment of the present invention, first comprises removing the damaged area from the composite structure. This may be done in a manner that is known to one of ordinary skill in the art. Next, the damaged area is prepared. In one embodiment, a resin may containing nanotubes may be applied to the damaged area and then removed through dissolution, or etching, with a predetermined solution. This exposes more of the fibers metal surface, and the increased surface area consequently increases the likelihood of establishing a low-resistance electrical contact with those fibers in the repair patch or the putty. Next, a composite patch containing nanotubes is sized to fit in the damaged area. In one embodiment, the nanotubes may be single-walled nanotubes ("SWNT"). In another embodiment, the nanotubes may be multiple-walled nanotubes ("MWNT").

The patch size may be the same size or larger than the size of the damaged area. In another embodiment, the patch size can be slightly smaller than the damaged area. In one embodiment, the patch may be applied to the damaged area with a resin that contains nanotubes. In another embodiment, putty containing electrically conductive nanotubes may be applied to the repair area. Depending on the chemical nature and requirements of the composite, the repair area can be cured preferably using heat, radiation such as UV radiation, a chemical curing agent, or by other means well known to those of ordinary skill in the art.

Other embodiments and uses of the invention will be apparent to those skilled in the art from consideration of the specification and practice of the invention disclosed herein. All references cited herein, including all U.S. and foreign patents and patent applications, all priority documents, all printed publications, and all government publications cited or referenced herein, for what ever reason, are specifically and entirely incorporated herein by reference.

U.S. Patent Application entitled "Coating Comprising Carbon Nanotubes and Methods for Forming Same", which is being filed contemporaneously herewith, including its priority document, Provisional Application No. 60/278,419, filed Mar. 26, 2001, are specifically and entirely incorporated herein by reference.

It is intended that the specification and examples be considered exemplary only, with the true scope and spirit of the invention indicated by the following claims.

What is claimed is:

1. A method for repairing a damaged composite structure wherein the damage decreased electrically conductivity of said structure comprising:

applying a patch to a damaged area wherein said patch contains a resin and carbon nanotubes that can provide an electrical connection between said patch and said composite structure sufficient to at least partially restore said decreased electrical conductivity;

further comprising the step of preparing the damaged area for repair, wherein the step of preparing comprises applying a resin to the damaged area wherein said resin contains electrically conductive fibers that will electrically interact with said patch;

applying a solvent to remove the resin, but not the electrically conductive fibers, such that said electrically conductive fibers remain on said damaged area to electrically interact with said patch.

2. The method of claim 1 wherein the patch is further comprised of a composite material.

3. The method of claim 1 wherein the patch is further comprised of a putty.

4. The method of claim 1 wherein the step of preparing comprises removing a damaged section from the damaged area and exposing a conductive layer surrounding the damaged area.

5. The method of claim 1 wherein the step of preparing comprises sizing the patch for the damaged area.

6. The method of claim 1 wherein the step of preparing comprises applying a putty to the damaged area.

7. The method of claim 1 further comprising the step of curing the patch.

8. The method of claim 7 wherein the step of curing comprises applying heat, radiation, a chemical curing agent or a combination thereof, to the damaged area.

9. A damaged composite structure repaired by the method of claim 1.

* * * * *